(12) United States Patent
Qian et al.

(10) Patent No.: US 10,060,878 B2
(45) Date of Patent: Aug. 28, 2018

(54) SYSTEM FOR RAPID ELECTROPHORESIS BINDING METHOD AND RELATED KITS AND COMPOSITIONS

(71) Applicant: Nanjingjinsirui Science & Technology Biology Corporation, Nanjing (CN)

(72) Inventors: Hong Qian, Nanjing (CN); Xin Chen, Nanjing (CN); Hongfei Ren, Nanjing (CN); Tao Bai, Nanjing (CN); Fang Liang Zhang, Fanwood, NJ (US)

(73) Assignee: NANJINGJINSIRUI SCIENCE & TECHNOLOGY BIOLOGY CORPORATION, Nanjing (CN)

( * ) Notice: Subject to any disclaimer, the term of this patent is extended or adjusted under 35 U.S.C. 154(b) by 507 days.

(21) Appl. No.: 14/706,113

(22) Filed: May 7, 2015

(65) Prior Publication Data

US 2015/0241388 A1    Aug. 27, 2015

Related U.S. Application Data

(63) Continuation of application No. 14/618,387, filed on Feb. 10, 2015, and a continuation-in-part of
(Continued)

(30) Foreign Application Priority Data

Nov. 29, 2012    (CN) .......................... 2012 1 0500785

(51) Int. Cl.
G01N 27/447    (2006.01)

(52) U.S. Cl.
CPC ..... *G01N 27/447* (2013.01); *G01N 27/44726* (2013.01); *G01N 27/44747* (2013.01); *G01N 27/44756* (2013.01)

(58) Field of Classification Search
CPC .......... G01N 27/447; G01N 27/44726; G01N 27/44747; G01N 27/44756
See application file for complete search history.

(56) References Cited

U.S. PATENT DOCUMENTS

| 3,966,897 A | 6/1976 | Renn et al. |
| 4,021,324 A | 5/1977 | Delony et al. |

(Continued)

FOREIGN PATENT DOCUMENTS

| CN | 1609608 A | 4/2005 |
| CN | 101034043 A | 9/2007 |

(Continued)

OTHER PUBLICATIONS

Office Action dated Apr. 26, 2016 in JP Application No. 2015-544333.
(Continued)

*Primary Examiner* — Maris R Kessel
(74) *Attorney, Agent, or Firm* — Panitch Schwarze Belisario & Nadel LLP

(57) ABSTRACT

An improved staining method and system is described for staining a biopolymer such as a peptide, a protein, an RNA, a DNA, an oligosaccharide or a complex containing a peptide, a protein, an RNA, a DNA, or an oligosaccharide in a matrix. The method includes the step of moving a staining reagent into the matrix using an electric force. The staining time can be dramatically reduced relative to conventional technologies. The improved staining method can particularly be used, for example, to stain proteins after gel separation. Other related methods, related kits and related systems for carrying out the staining method are also described.

4 Claims, 5 Drawing Sheets

Related U.S. Application Data application No. PCT/CN2013/086826, filed on Nov. 11, 2013, which is a continuation-in-part of application No. 12/797,011, filed on Jun. 9, 2010, now Pat. No. 8,968,541.

(60) Provisional application No. 61/302,213, filed on Feb. 8, 2010, provisional application No. 61/221,230, filed on Jun. 29, 2009.

(56) References Cited

U.S. PATENT DOCUMENTS

| | | | |
|---|---|---|---|
| 4,693,804 A | | 9/1987 | Serwer |
| 5,559,032 A | | 9/1996 | Pomeroy et al. |
| 5,922,186 A | * | 7/1999 | Shukla ............. G01N 27/44704 204/462 |
| 6,277,259 B1 | | 8/2001 | Guttman et al. |
| 6,319,720 B1 | | 11/2001 | Wondrak |
| 2004/0050699 A1 | * | 3/2004 | Goncalves ....... G01N 27/44704 204/450 |
| 2006/0275917 A1 | | 12/2006 | Wada |
| 2010/0041045 A1 | | 2/2010 | Rueck et al. |
| 2010/0326828 A1 | | 12/2010 | Wang et al. |

FOREIGN PATENT DOCUMENTS

| | | |
|---|---|---|
| CN | 101936837 A | 1/2011 |
| CN | 201917487 U | 8/2011 |
| CN | 102607920 A | 7/2012 |
| CN | 102749369 A | 10/2012 |
| EP | 1406089 A1 | 4/2004 |
| JP | 56-69550 A | 6/1981 |
| JP | 62-167430 A | 7/1987 |
| JP | 2005257652 A | 9/2005 |
| JP | 2007010649 A | 1/2007 |
| WO | 2004/011926 A1 | 2/2004 |
| WO | 2004104557 A2 | 12/2004 |

OTHER PUBLICATIONS

Fazekas et al, "Two new staining procedures for quantitative estimation of proteins on electrophoretic strips", Biochim. Biophys. Acta., vol. 71, pp. 377-391 (1963).

ISR/WO dated Feb. 27, 2014 in PCT/CN2013/086826.

Extended European Search Report dated Jul. 7, 2016 in EP Application No. 13857824.0.

* cited by examiner

Fix for 1 hr   Stain for 1 hr   Destain for 3 hrs

Quick staining for 6 minutes

SYSTEM FOR RAPID ELECTROPHORESIS BINDING METHOD AND RELATED KITS AND COMPOSITIONS

CROSS-REFERENCE TO RELATED APPLICATIONS

This application is a Continuation-in-part of International Application No. PCT/CN2013/086826 filed in China on Nov. 11, 2013, which was published in the Chinese language on Jun. 5, 2014, under International Publication No. WO 2014/082525, and the disclosure of which is hereby incorporated by reference in its entirety. This application is also a Continuation of U.S. patent application Ser. No. 14/618,387, filed Feb. 10, 2015, which is a Continuation-in-part of U.S. patent application Ser. No. 12/797,011, filed Jun. 9, 2010, now U.S. Pat. No. 8,968,541 issued on Mar. 3, 2015, which is entitled to and claims the benefit of the priority pursuant to 35 U.S.C. § 119(e) of U.S. Provisional Patent Application No. 61/221,230, filed Jun. 29, 2009, and U.S. Provisional Patent Application No. 61/302,213, filed Feb. 8, 2010, the disclosures of which are hereby incorporated by reference in their entireties.

FIELD OF THE INVENTION

The invention relates to a system and method for rapidly binding a binding agent to a biopolymer such as a peptide, a protein, an RNA, a DNA, an oligosaccharide or a complex thereof in a matrix by moving the binding agent into the matrix using an electric force, thereby binding the binding agent to the biopolymer in the matrix. In a particular embodiment, the invention relates to systems and kits and compositions useful for performing rapid staining of proteins or peptides resolved by polyacrylamide gel electrophoresis (PAGE).

BACKGROUND OF THE INVENTION

The technique used to separate charged particles based on a difference in their migration speeds through an electric field is referred to as electrophoresis. The electrophoretic mobility of a charged particle is the distance the charged particle migrates within an electric field over a unit of time. Charged particles will separate, as their migration distances are different, as a result of different charges or mass-to-charge ratios, when they are placed in the same electric field for a certain time. In 1937, Swedish researcher A. W. K. Tiselius designed the first electrophoresis apparatus for moving boundary electrophoresis, which was used to separate three globulins from horse serum. New electrophoretic techniques continued to be developed thereafter from the 1940s to early 1950s, based on different electrophoretic matrices, such as filter paper, CM-cellulose, and agar. In the late 1950s, starch gel electrophoresis and polyacrylamide gel electrophoresis were also developed. Currently, electrophoretic techniques are widely used in the field of analytical chemistry, biochemistry, clinical chemistry, pharmacology, immunology, microbiology, and genetics.

Biopolymers such as peptides, proteins, nucleic acids (RNA or DNA), oligosaccharides, or complexes thereof are commonly analyzed by gel electrophoresis. Usually samples of interest are loaded in a matrix such as a polyacrylamide gel and exposed to an electric field which causes various components in the sample to migrate and separate into distinct bands according to the molecular weight, net charge, size, and other physical and chemical properties of the molecules and the pore size of the matrix. After electrophoresis, different biopolymers embedded at different locations on the matrix can be further characterized by their interactions with or bindings to one or more binding agents, such as staining reagents.

Numerous methods and reagents have been developed to visualize or detect the biopolymers of interest within a matrix such as a gel. These include staining reagents that can be classified into five classes. The first class of staining reagents includes organic dyes that bind to biopolymers, such as Coomassie Blue dyes that stain proteins and make the protein bands blue, which can be subsequently visualized by naked eyes. The second class of staining reagents includes fluorescent dyes that bind to biopolymers, such as ethidium bromide that stains DNA or RNA and makes the stained DNA or RNA bands red when shined with UV light. The third class of staining reagents includes silver staining reagents. The fourth class of staining reagents includes staining reagents that stain the background, which are also called negative staining reagents. The fifth class of staining reagents includes biological molecules and their derivatives, such as antibodies and antibody-based reagents that bind to antigens, which are also called immunostaining reagents, or labeled polynucleotide that binds to complementary DNA or RNA. The second and third classes of staining reagents were developed to increase the sensitivity over that achieved with the organic dyes of the first class.

Coomassie Blue staining was introduced in early 1960s by Fazekas, et al. as a method for visualizing proteins in the gels (*Biochim. Biophys. Acta* 71:377, 1963). In addition to Coomassie Blue, other organic dyes such as Amido black, Ponceaus S, Fast green FCF, zincon, Eriochrome black T, etc., have also been used to stain proteins. However, Coomassie Blue staining is still widely used and remains the most commonly used general method for protein staining and detection.

Typically, a conventional method for Coomassie Blue staining of proteins embedded in a gel comprises the following steps: (i) fixing the gel in Fixing Solution for 1 hour (hr) with gentle agitation; (ii) staining the gel from Step (i) in Staining Solution for 1 hr with gentle agitation; and (iii) destaining the gel from Step (ii) in Destaining Solution. The Destaining Solution is replaced several times during the destaining step until the background of the gel is fully destained, which usually takes 2 to 3 hours or even overnight.

Staining proteins with organic dyes is relatively inexpensive, takes less time than silver staining, but it still takes a few hours or even overnight. For example, the above described conventional method of Coomassie Blue staining takes about 3 hours or more with at least 3 steps, thus is time consuming and cumbersome. Improvements have been made in Coomassie Blue protein staining methods, e.g., by using new staining reagents such as Colloidal Coomassie Blue, or by performing the incubation in a microwave to enhance staining and reduce the incubation time. However, the three basic steps of fixing, staining and destaining are still necessary to obtain satisfactory results.

Immunostaining of antigens in a matrix, such as a polyacrylamide gel, also takes many steps and multiple solutions. Each step may take minutes to hours to complete, in part because the staining reagents, e.g., antibodies and antibody-based reagents, diffuse into the matrix slowly. Similarly, the hybridization of a polynucleotide with another polynucleotide, such as the Southern or Northern blotting, is also time consuming.

Thus, there is still a need for a simple and rapid process for staining a biopolymer, such as a peptide, a protein, an RNA, a DNA, an oligosaccharide or a complex thereof. There is also a need for systems that can be used to provide for quick, efficient, and sensitive detection of biopolymers. Embodiments of the present invention relate to such systems and processes for staining, and thus detection, of biopolymers embedded in a matrix with reduced time and costs.

BRIEF SUMMARY OF THE INVENTION

It is now discovered that an electric force can be used to move a binding agent, such as a staining reagent, into a matrix embedded with a biopolymer to thus bind the binding agent to the biopolymer in the matrix, stain or label the biopolymer with significantly reduced time and costs. In addition to improved methods for staining or labeling a biopolymer in a matrix, the present invention also relates to systems and kits for quick, efficient, and sensitive detection of biopolymers that provide for implementation of methods according to the invention.

The binding method can be performed with a binding system interposed between a positive electrode and a negative electrode. The electric force moves a binding agent, such as a staining reagent, through the matrix, and the binding agent collides with, thus reacts with or binds to, a biopolymer embedded in the matrix, thus staining or labeling the biopolymer. The voltage applied to the electrodes can be adjusted for quick movement of the binding agent to significantly reduce the incubation time needed for its binding to the biopolymer.

According to embodiments of the present invention, the three steps of the conventional method of Coomassie Blue protein staining, i.e., the fixing, staining and destaining steps described above, are now accomplished by a single step, i.e., applying an electric force to the staining reagent. The electric force moves the staining reagent into the polyacrylamide gel to thus stain the protein in the gel, and further moves the free excess staining reagent out of the polyacrylamide gel to thus destain the gel. The time required for Coomassie Blue protein staining is now reduced to less than 10 minutes. In addition to protein staining, such method is also applicable for the interacting, reacting, binding or staining of other target molecules.

In one general aspect, the present invention relates to an integrated method for interacting a charged molecule with a target molecule. The method comprises moving the charged molecule with an electric force into a matrix embedded with the target molecule, so that the charged molecule interacts with the target molecule in the matrix.

Another general aspect of the present invention relates to an integrated method for reacting a charged molecule with a target molecule. The method comprises moving the charged molecule with an electric force into a matrix embedded with the target molecule, so that the charged molecule reacts with the target molecule in the matrix.

Another general aspect of the present invention relates to an integrated method for binding a charged molecule to a target molecule. The method comprises moving the charged molecule with an electric force into a matrix embedded with the target molecule, so that the charged molecule binds to the target molecule in the matrix.

Yet another general aspect of the invention relates to an integrated method for staining a target molecule with a charged molecule. The method comprises moving the charged molecule with an electric force into a matrix embedded with the target molecule, so that the charged molecule stains the target molecule in the matrix.

In one general aspect, the present invention relates to a method of binding a binding agent to a biopolymer embedded in a matrix. The method comprises applying an electric force to a binding agent to move the binding agent into the matrix, thereby binding the binding agent to the biopolymer embedded in the matrix, and to move excess free binding agent out of the matrix.

In one particular embodiment, the present invention relates to a method of staining a biopolymer embedded in a matrix. The method comprises applying an electric force to a staining reagent to move the staining reagent into the matrix, thereby staining the biopolymer embedded in the matrix with the staining reagent, and to move excess free staining reagent out of the matrix, thereby destaining the matrix.

In an embodiment of the presently described method of binding a binding agent to a biopolymer embedded in a matrix, the method comprises:
  assembling a binding system comprising:
    (i) a first solid porous material absorbed with a binding solution comprising a binding agent;
    (ii) the matrix embedded with the biopolymer; and
    (iii) optionally one or more solid porous materials absorbed with one or more buffer solutions,
  interposing the binding system between a pair of electrodes; and
  connecting the pair of electrodes to a power supply for establishing an electric force sufficient to move the binding agent into the matrix, thereby binding the binding agent to the biopolymer in the matrix, and to move excess free binding agent out of the matrix.

In an embodiment of the presently described method of staining a biopolymer embedded in a matrix, the method comprises:
  assembling a staining system comprising:
    (i) a first solid porous material absorbed with a staining solution comprising a staining reagent;
    (ii) the matrix embedded with the biopolymer; and
    (iii) optionally one or more solid porous materials absorbed with one or more buffer solutions,
  interposing the staining system between a pair of electrodes; and
  connecting the pair of electrodes to a power supply for establishing an electric force sufficient to move the staining reagent into the matrix, thereby staining the biopolymer in the matrix, and to move excess free staining reagent out of the matrix, thereby destaining the matrix.

Another general aspect of the present invention relates to a system for staining a target molecule with a staining reagent. In one embodiment of the present invention, the system comprises:
  (i) a matrix to be embedded with a target molecule to form a matrix embedded with the target molecule;
  (ii) a first solid porous material for forming a first solid porous material absorbed with a staining solution comprising a staining reagent, wherein the first solid porous material absorbed with the staining solution is to be placed in contact with the matrix embedded with the target molecule;
  (iii) a pair of electrodes for applying an electric force sufficient to move the staining reagent from the first solid porous material into the matrix embedded with the target molecule, thereby staining the target molecule, and to move excess free staining reagent out of the matrix, thereby destaining the matrix; and (iv) optionally, one or more additional solid porous materials absorbed with one or more buffer solutions.

In a particular embodiment of the present invention, the system further comprises a kit for staining the target molecule with a staining reagent, the kit comprising:
(i) a staining solution comprising a staining reagent;
(ii) a plurality of solid porous materials;
(iii) optionally one or more buffer solutions;
(iv) optionally one or more matrices for embedding a target molecule; and
(v) instructions for using the staining solution and optionally the buffer solutions for staining the biopolymer in the matrix utilizing an electric force applied to the staining reagent.

In one embodiment of the present invention, the staining solution or the optional one or more buffer solutions are pre-absorbed in one or more solid porous materials, and the pre-absorbed solid porous materials are provided in the kit.

According to a particular embodiment of the present invention, a system for staining a target molecule with a staining reagent comprises, in the following order:
(i) a first solid porous material absorbed with a staining solution comprising a staining reagent;
(ii) a matrix embedded with a target molecule;
(iii) a second solid porous material absorbed with an electrolytic buffer; and
(iv) a pair of electrodes for applying an electric force sufficient to move the staining reagent from the first solid porous material into the matrix embedded with the target molecule, thereby staining the target molecule, and to move excess free staining reagent out of the matrix, thereby destaining the matrix,
wherein the pair of electrodes are to be connected to the first solid porous material and second solid porous material, respectively.

In another embodiment of the present invention, a system for staining a target molecule with a staining reagent comprises:
(i) a matrix to be embedded with a target molecule to form a matrix embedded with the target molecule;
(ii) a staining reservoir for receiving the matrix embedded with the target molecule;
(iii) one or more pumps to be connected to the staining reservoir for pumping a staining solution comprising a staining reagent into and out of the staining reservoir, and for pumping a washing buffer into and out of the staining reservoir; and
(iv) a pair of electrodes for applying an electric force sufficient to move the staining reagent from the staining solution that is pumped into the staining reservoir into the matrix embedded with the target molecule, thereby staining the target molecule, and to move excess free staining reagent out of the matrix into the washing buffer that is pumped into the staining reservoir, thereby destaining the matrix.

According to embodiments of the present invention, the system can further comprise a waste collection unit to be connected to the staining reservoir for receiving the staining solution and destaining buffer that is pumped out of the staining reservoir.

In certain embodiments of the present invention, the system for staining a target molecule with a staining reagent is an automated system. According to embodiments of the present invention, an automated system further comprises an automated control unit connected to the pair of electrodes, wherein the automated control unit comprises one or more components selected from the group consisting of a display panel, a power supply, and a power switch.

Yet another general aspect of the present invention relates to a kit for binding a binding agent to a biopolymer. In a particular embodiment, the present invention relates to a kit for staining a biopolymer. According to embodiments of the present invention, the kit comprises:
a staining solution comprising a staining reagent;
optionally one or more buffer solutions; and
instructions for using the staining solution and optionally the buffer solutions for staining the biopolymer in the matrix utilizing an electric force applied to the staining reagent.

The binding agent or staining reagent can be any type of reagent suitable for the present invention, including, but not limited to, an organic or inorganic reagent, a dye or a dye-labeled reagent, a fluorescent molecule, a radioactive or radioactive-labeled reagent, an antibody or an antibody-based reagent, a labeled polypeptide or ligand, or a labeled polynucleotide.

The matrix used in embodiments of the present invention can be composed of any type of matrix material suitable for the present invention, including, but not limited to, an agarose gel, polyacrylamide gel, or any other suitable porous materials.

The biopolymer is selected from the group consisting of a peptide, a protein, an RNA, a DNA, an oligosaccharide, and a complex thereof. It is understood by those skilled in the art that modified biopolymers or derivatives of biopolymers can also be readily labeled or stained, thus detected, by the present methods in view of the present disclosure.

According to certain embodiments of the present invention, the biopolymer is a protein or peptide, the matrix is a sodium dodecyl sulfate or native polyacrylamide gel, and the staining reagent is a polypeptide-staining reagent selected from the group consisting of an organic dye, an inorganic dye, a fluorescent dye, a metal-complex dye, an antibody, and a labeled polypeptide or ligand, and the polypeptide-staining reagent is absorbed in a solid porous material.

In a particular embodiment of the present invention, the biopolymer is a protein or peptide, the matrix is polyacrylamide gel, and the staining reagent is Coomassie Blue.

In another particular embodiment of the present invention, the biopolymer is a protein or peptide, the matrix is polyacrylamide gel, and the staining reagent is an antibody or an antibody-based reagent.

Embodiments of the present invention also relate to staining a biopolymer embedded in a matrix with two or more staining reagents.

The details of embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

In the drawings.

DETAILED DESCRIPTION OF THE INVENTION

Figure 1:
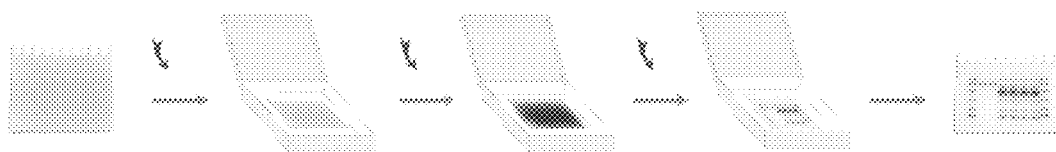
FIG. 1 schematically illustrates a conventional Coomassie Blue staining procedure.

Unless defined otherwise, all technical and scientific terms used herein have the same meaning as is commonly understood by one of skill in the art to which this invention belongs. All publications and patents referred to herein are incorporated by reference.

Embodiments of the present invention relate to methods, kits, systems, and compositions useful for rapid staining of biopolymers in a matrix. In one aspect, the invention relates to a significant improvement of the conventional biopolymer staining techniques. For example, the present invention provides an improved protein staining method whereby several steps in the conventional Coomassie Blue staining procedure are reduced to one step.

According to embodiments of the present invention, an electric force moves a charged staining reagent into a matrix embedded with a biopolymer via a positive electrode and a negative electrode connected to a staining system. Depending on the voltage applied on the two electrodes, the electric force can move the staining reagent much faster than diffusion that governs the movement of the staining reagent in the conventional staining methods. The electric force can not only facilitate the quick movement of the staining reagent into the matrix to label or stain the embedded biopolymer, but also facilitate the quick movement of the excess free staining reagent out of the matrix to thereby destain the matrix. Therefore, methods according to embodiments of the present invention greatly reduce the time for staining, and thus detection, of a biopolymer, at significantly reduced costs.

As used herein, the terms "binding", a "binding agent", "staining", a "staining reagent", a "biopolymer", and a "matrix" are to be taken in their broadest context.

As used herein, the terms "binding" or "bind" refer to an interaction between a binding agent and a target molecule, such as a biopolymer, that results in a stable association in which the binding agent and the target molecule are in close proximity to each other. In the stable association, the binding agent and the target molecule can be interacting with each other non-covalently and/or covalently, the binding agent and the target molecule can be unmodified, the binding agent and the target molecule can also be modified as a result of a chemical reaction occurred during the binding process. Examples of the binding interactions include, but are not limited to, biopolymer-staining reagent interaction, protein-protein interaction, protein-peptide interaction, protein-antibody interaction, protein-small molecule interaction, protein-polynucleotide interaction, polynucleotide-polynucleotide interaction, etc.

As used herein, the term "binding agent" refers to any agent that can bind to a target molecule. The binding agent is movable by an electric force in a matrix. Examples of the binding agent to a biopolymer include, but are not limited to, a staining reagent, another biopolymer, an organic molecule, an inorganic molecule, etc.

As used herein, the term "staining" refers to a process in which a staining reagent reacts with, covalently or non-covalently binds to, or otherwise labels a biopolymer for the visualization, detection, or otherwise qualification or quantification of the biopolymer. The term "staining" encompasses "labeling", although it is not limited to "labeling."

A "staining reagent" refers to any reagent that can be used to stain or label a biopolymer by any mechanism. The staining reagent is movable by an electric force in a matrix. For example, a "staining reagent" can stain a biopolymer by a chemical reaction with the biopolymer. It can also stain the biopolymer by binding to the biopolymer, covalently or non-covalently. A "staining reagent" can be any colored or colorless substance that is detectable by a detection method. For example, a staining reagent includes, but is not limited to, an organic dye, an inorganic dye, a fluorescent dye, a metal-complex dye, a radioactive or radioactive-labeled molecule, or a colorless substance that changes color, becomes fluorescent, or otherwise becomes detectable after it binds to the biopolymers. A staining reagent can be in a pure form, or it can also exist in a mixture or solution. A staining reagent can be in a modified form (e.g., modified by a chemical) or unmodified form. The staining reagents also include a biological molecule or derivative thereof, such as an antibody or an antibody-based reagent used for immunostaining, a peptide used in ligand binding, a polynucleotide using in nucleotide hybridization, etc.

A "biopolymer" includes, but is not limited to, a peptide, a protein, an RNA, a DNA, an oligosaccharide, a complex thereof, or a modification or derivative thereof. Examples of the complex include, but are not limited to, a polypeptide-polypeptide complex, an RNA-polypeptide complex, a DNA-polypeptide complex, a polynucleotide-polynucleotide complex, etc.

In one general aspect, the present invention relates to a method of staining a biopolymer embedded in a matrix with reduced steps and time as compared to the conventional staining method. For example, as illustrated in FIG. 1, the conventional protein staining method is usually comprised of the three steps, i.e., a fixing step, a staining step and a washing step. Each of these steps is necessary in the conventional protein staining in order to obtain acceptable results. In contrast, an embodiment of the present invention provides a staining method whereby the three steps of conventional staining are combined into one step, with the use of an electric force that moves the staining reagent into the matrix, thereby staining the biopolymer, such as a protein, embedded in the matrix, and to move excess free staining reagent out of the matrix, thereby destaining the matrix. The method according to the embodiment of the present invention has greatly cut down the time required for biopolymer staining.

Embodiments of the invention relate to compositions useful in biopolymer staining One of the compositions is a staining solution, i.e., a solution comprising one or more staining reagents.

In one embodiment of the invention, a staining solution comprises, for example, Coomassie Blue, sodium phosphate, potassium chloride, isopropanol, Tris, EDTA and acetic acid. Each of these elements can be substituted with similar elements known in the art that function in a solution in substantially the same way. Isopropanol, for example can be substituted with methanol or ethanol or other agents known in the art. Coomassie Blue can be substituted with one or more other protein staining dyes such as Amido black, Ponceaus S, Fast green FCF, zincon, Eriochrome black T, etc.

In one embodiment of the invention, the staining solution comprises about 0.1 gram to 5 grams, typically about 1 gram, Coomassie Blue (either R-250 or G-250) per liter of the staining solution.

In another embodiment of the invention, the staining solution comprises about 10 grams to 500 grams, typically about 200 grams, isopropanol per liter of the staining solution.

In yet a further embodiment of the invention, the staining solution comprises about 10 grams to about 300 grams, typically about 150 grams, acetic acid per liter of the staining solution.

In yet a further embodiment, the staining solution comprises about 0.1 gram to about 10 grams, typically about 1 gram, EDTA per liter of the staining solution.

In yet a further embodiment, the staining solution comprises about 0.1 gram to about 10 grams, typically about 1 gram, Tris per liter of the staining solution.

In yet a further embodiment, the staining solution comprises about 0.1 gram to about 10 grams, typically about 1 gram, sodium chloride per liter of the staining solution.

In yet a further embodiment, the staining solution comprises about 0.1 gram to about 10 grams, typically about 1 gram, sodium phosphate per liter of the staining solution.

In one embodiment, the pH of the staining solution is in the range of about 2.0-about 11.0, typically about 5.0.

A staining solution according to embodiments of the invention can be bottled and used as typically done in research and diagnostic laboratories. It can also be pre-absorbed in a solid porous material, such as a piece of filter paper, blotting paper, a pad, e.g., paper pad, or the like. The staining solution can be included in an article of manufacture or kit for use in biopolymer staining, such as in protein staining, and the like.

Other solutions can also be used in addition to the staining solution described above in view of the present disclosure. One or more of the ingredients in the staining solution can be omitted. On the other hand, one or more of other reagents can be added to the staining solution. The purpose of the staining solution is to improve the staining efficiency, which allows combining the fixing step, staining step and destaining step into a single step. Other solutions which serve similar functions can be developed and used in view of the present disclosure.

Other staining reagents can also be used to stain proteins in addition to the staining reagent illustrated above, such as Coomassie Blue, either R-250 or G-250. These other staining reagents include, but are not limited to, Amido black, Ponceaus S, Fast green FCF, zincon, Eriochrome black T, calconcarboxylic acid, methyl violet, Meldola's blue, methyl orange, Fast green, Ferrozine, Ferene S, etc.

Fluorescent staining reagents can also be used to stain proteins. These fluorescent staining reagents include, but are not limited to, Rhodamine, Sypro series, Deep Purple, etc. It is noted that some staining reagents can become fluorescent before or after binding to proteins.

Metal ion or metal-complex (also called metal chelates) staining reagents can also be used to stain proteins. These staining reagents include, but are not limited to, Ferrocyanide, indium- or molybdenum-pyrogallol red complex, or other metal complexes formed with pyrocatechol violet, bromopyrogallol red, xylenol orange, pyrogallol phthalein, etc. It should be noted that some of this kind of staining reagents are fluorescent or will become fluorescent after binding to proteins.

Antibodies or antibody-binding or antibody-based reagents can also be used to stain proteins by immunostaining. These staining reagents include, but are not limited to, primary antibodies, secondary antibodies, Protein A, Protein G, Protein L, Protein A/G, tag or reporter molecule-labeled primary antibodies, secondary antibodies, Protein A, Protein G, Protein L, Protein A/G. Tag or reporter molecules include, but are not limited to, horseradish peroxidase (HRP), alkaline phosphate (AP), beta-galactosidase or other enzymes, radioactive isotope of iodine or other isotopes, fluorochromes which can be detected by fluorescence microscope or fluorometer, luminochromes which can be detected by luminescence methods.

A labeled peptide or ligand can also be used to label a binding partner or receptor for the peptide or ligand embedded in a matrix. Preferably, the matrix is a native polyacrylamide gel.

It is apparent to those skilled in the art that the present invention includes modifications to the above-mentioned embodiments to further improve the staining sensitivity. These modifications include, but are not limited to, adding one or multiple steps to the above embodiment. For example, one can add a destaining step to further decrease background when higher sensitivity is desired.

In another general aspect, the present invention also provides systems for implementing the quick staining assay and methods for staining a target molecule according to embodiments of the invention. However, a variety of methods can be used to set up the quick staining assays in view of the present disclosure.

In some embodiments of the present invention, a system for staining a target molecule with a staining reagent comprises a solid porous material absorbed with a staining solution comprising a staining reagent, and a pair of electrodes for applying an electric force sufficient to move the staining reagent out of the solid porous material and into the matrix embedded with a target molecule, thereby staining the target molecule. In other embodiments of the present invention, a system comprises a staining reservoir for receiving a matrix embedded with a target molecule, one or more pumps to be connected to the staining reservoir for pumping a staining solution comprising a staining reagent into the staining reservoir, and a pair of electrodes for applying an electric force sufficient to move the staining reagent from the staining solution into the matrix embedded with a target molecule, thereby staining the target molecule.

According to embodiments of the present invention, a system for staining a target molecule with a staining reagent comprises:
(i) a matrix to be embedded with a target molecule to form a matrix embedded with the target molecule;
(ii) a first solid porous material for forming a first solid porous material absorbed with a staining solution comprising the staining reagent, wherein the first solid porous material absorbed with the staining solution is to be placed in contact with the matrix embedded with the target molecule;
(iii) a pair of electrodes for applying an electric force sufficient to move the staining reagent from the first solid porous material into the matrix embedded with the target molecule, thereby staining the target molecule, and to move excess free staining reagent out of the matrix, thereby destaining the matrix; and
(iv) optionally, one or more additional solid porous materials absorbed with one or more buffer solutions.

According to embodiments of the present invention, the system can further comprise a staining reservoir for receiving both a matrix embedded with the target molecule and a first solid porous material absorbed with a staining solution. The staining reservoir can further contain a buffer. An electric force applied by the pair of electrodes moves the staining reagent into the matrix thereby staining the target molecule embedded in the matrix. The electric force is also sufficient to move the excess free staining reagent out of the matrix, thereby destaining the matrix.

According to embodiments of the present invention, a solid porous material can be a blotting paper, filter paper, or any other porous material capable of being absorbed with a staining solution and/or one or more buffer solutions. In a particular embodiment, the solid porous material is a blotting paper having a thickness of about 0.1 mm to about 20 mm. According to embodiments of the present invention, the solid porous material absorbed with the staining reagent can further be absorbed with an electrolytic buffer solution. In other embodiments, additional solid porous materials absorbed with one or more buffer solutions can be included in the system.

According to preferred embodiments of the invention, the staining reagent is an organic dye selected from the group consisting of Coomassie Blue, Amido black, Ponceaus S, Fast green FCF, zincon, Eriochrome black T, Colloidal Coomassie Blue, and derivatives thereof.

Systems according to embodiments of the present invention can be used to stain a target molecule embedded in a matrix with one staining reagent or with multiple staining reagents. For example, the first solid porous material can be further absorbed with a second staining solution comprising a second staining reagent, wherein the staining reagent and second staining reagent have the same charge type. Other embodiments include systems further comprising an additional solid porous material absorbed with a second staining solution comprising a second staining reagent, wherein the staining reagent and second staining reagent have the same charge type; and systems further comprising an additional solid porous material absorbed with a second staining solution comprising a second staining reagent, wherein the staining reagent and second staining reagent have opposite charge types.

According to embodiments of the present invention, a staining system is assembled and interposed between a pair of electrodes. Such staining system can comprise, for example:
(i) a solid porous material absorbed with a staining solution comprising a staining reagent;
(ii) a matrix embedded with a biopolymer; and
(iii) optionally one or more solid porous materials absorbed with one or more buffer solutions.

After the staining system is interposed between a pair of electrodes, the electrodes are connected to a power supply for establishing an electric force sufficient to move the staining reagent into the matrix, thereby staining the biopolymer in the matrix, and to move excess free staining reagent out of the matrix, thereby destaining the matrix.

Figure 5:
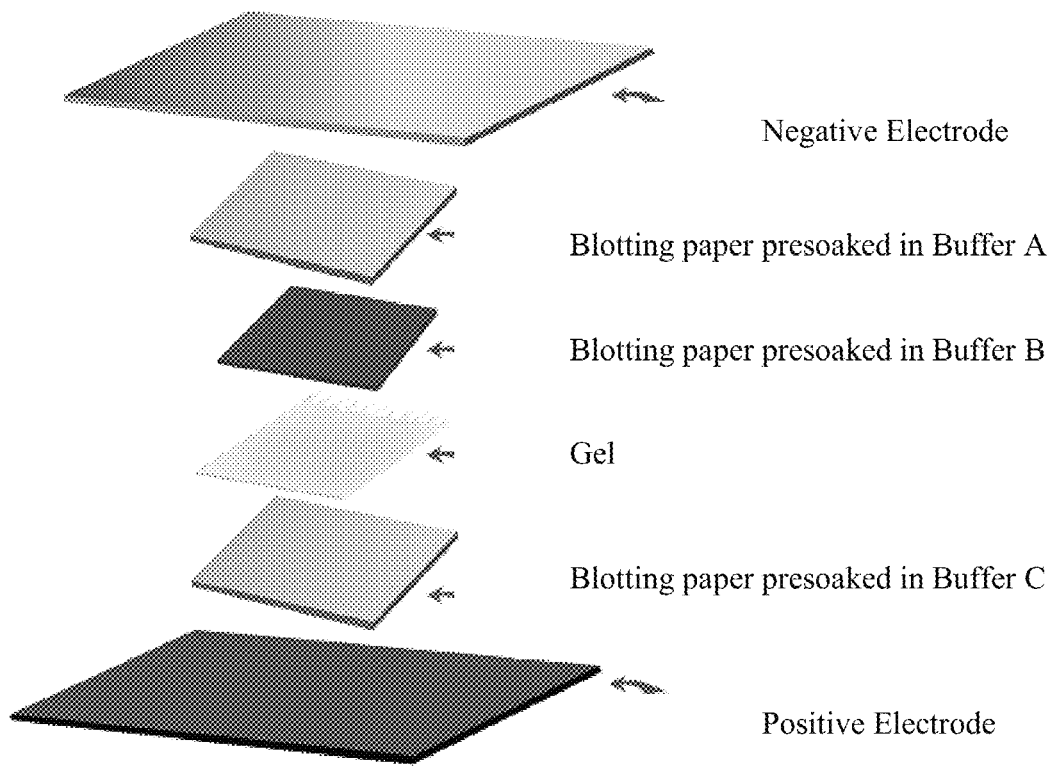
FIG. 5 schematically illustrates the sandwich setup of a quick Coomassie Blue staining procedure according to an embodiment of the invention.
Figure 6:
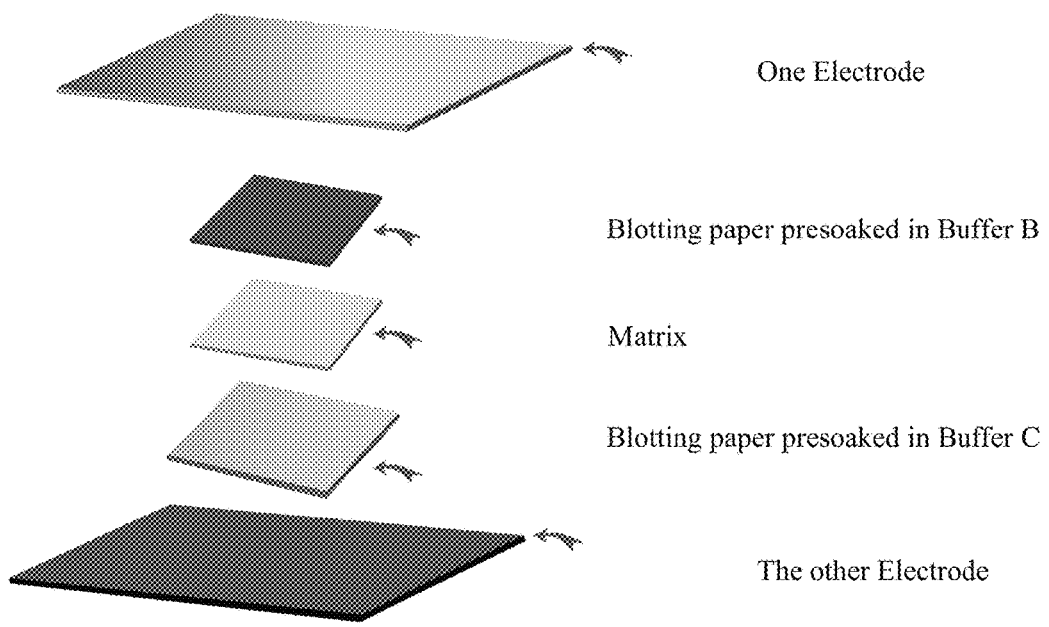
FIG. 6 schematically illustrates the sandwich setup of a quick Coomassie Blue staining procedure according to another embodiment of the invention.

According to embodiments illustrated in FIGS. 5 and 6, the staining reagent according to an embodiment of the present invention is pre-absorbed in a piece of blotting paper and placed on top of a gel embedded with proteins to be stained. If the staining reagent is positively charged, it can be pre-absorbed in a piece of blotting paper and placed just under the gel to be stained. When the electricity is turned on, the positively charged staining reagent will move up into the gel matrix and stain the proteins embedded there. It should be noted that a mixture of different staining reagents can also be used to improve staining sensitivity. It is also feasible to use the negatively charged staining reagent or mixture and the positively charged staining reagent or mixture at the same time, i.e., by separating the negatively charged staining reagent and the positively charged staining reagent with the gel matrix before staining.

In the above-mentioned embodiments, those skilled in the art will know that there are a variety of methods to position the two electrodes in view of the present disclosure. In the embodiment shown in FIG. 5, the positive electrode is at the bottom, while the negative electrode is on the top. The positions of the two electrodes can be switched. However, the position of the staining reagent should also be changed so that staining reagent will move into the gel matrix and stain the proteins. The voltage of the electricity applied to the staining apparatus can vary from 1 to 50 V.

In a preferred embodiment, the electric force moves the staining reagent in a direction that the free excess staining reagent enters the matrix and travels the least distance in the matrix before it leaves the matrix as compared to the other directions. For example, in FIG. 5, the staining reagent in Buffer B is moved into the gel in a direction transverse to the gel surface and travels a distance equal to the thickness of the gel before it leaves the gel. The thickness of the gel is the smallest compared to the other dimensions, e.g., length and width, of the gel.

However, the electric force can also move the staining reagent in other directions according to embodiments of the present invention.

Figure 2:
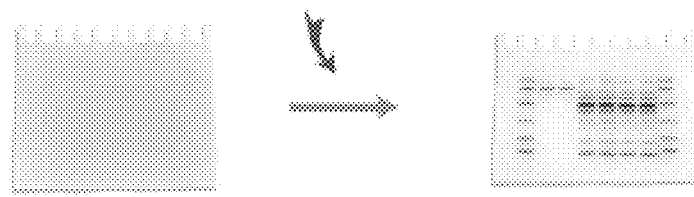
FIG. 2 schematically illustrates a quick Coomassie Blue staining procedure according to an embodiment of the invention.
Figure 3:
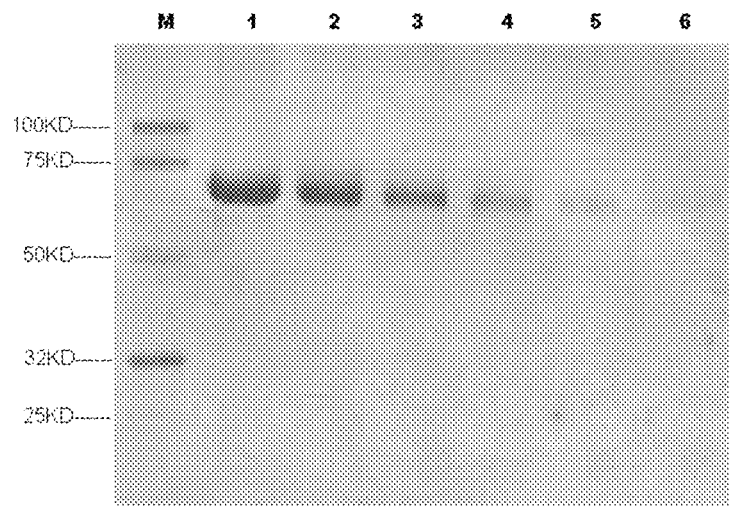
FIG. 3 is a picture of a SDS-PAGE gel after the quick Coomassie Blue staining procedure of FIG. 2; the gel is embedded with protein markers (GenScript MM0900; Lane M) and BSA protein at 1500 ng, 750 ng, 300 ng, 150 ng, 75 ng and 30 ng, in lanes 1 to 6, respectively.

A target molecule, such as a biopolymer, can be embedded in a matrix by any method known in the art in view of the present disclosure. In one embodiment of the present invention, the biopolymer is embedded in the matrix by electrophoresis, i.e., by applying an electrophoresis-electric force to the biopolymer to thus move it into the matrix, thereby embedding the biopolymer in the matrix. For example, as shown in FIGS. 2 and 3, a protein can be embedded in a polyacrylamide gel by loading a sample containing the protein into a loading well, applying an electric force to the protein to thus move the protein into the gel.

In embodiments according to FIGS. 5 and 6, the electric force used to embed the protein in the gel is transverse to the electric force used to move the staining reagent into the gel.

According to other embodiments of the present invention, a system for staining a target molecule with a staining reagent comprises:
(i) a matrix to be embedded with a target molecule to form a matrix embedded with the target molecule;
(ii) a staining reservoir for receiving the matrix embedded with the target molecule;
(iii) one or more pumps to be connected to the staining reservoir for pumping a staining solution comprising a staining reagent into and out of the staining reservoir, and for pumping a washing buffer into and out of the staining reservoir; and (iv) a pair of electrodes for applying an electric force sufficient to move the staining reagent from the staining solution that is pumped into the staining reservoir into the matrix embedded with the target molecule, thereby staining the target molecule, and to move the excess free staining reagent out of the matrix into the washing buffer that is pumped into the staining reservoir, thereby destaining the matrix.

According to embodiments of the present invention, a staining solution is pumped into the staining reservoir by a pump, and the target molecule is stained with a staining reagent in the staining solution by an electric force that moves the staining reagent from the staining solution into the matrix embedded with the target molecule. The electric force also moves the excess free staining reagent out of the matrix to destain the matrix. A washing buffer can also be pumped into the staining reservoir subsequent to the staining solution to aid in destaining of the matrix, wherein the excess free staining reagent is moved out of the matrix by the electric force and into the washing buffer that is pumped into the staining reservoir. According to this embodiment of the present invention, a target molecule can be stained with a staining reagent without the need for a solid porous material absorbed with a staining solution comprising the staining reagent. One of ordinary skill in the art would be able to determine appropriate parameters, such as pump flow rate and timing for introducing the washing buffer into the staining reservoir in order to achieve optimal results in staining the target molecule embedded in the matrix.

According to embodiments of the present invention, a system can further comprise a waste collection unit. The waste collection unit can be connected to the staining reservoir for receiving the staining solution and washing buffer that is pumped out of the staining reservoir. The waste collection unit can further be connected to a filtration unit, such as an activated charcoal filtration column or membrane. For example, the excess staining reagent that is pumped out of the staining reservoir for collection in the waste collection unit can be absorbed by the activated charcoal, such that the solution appears colorless.

Figure 7:
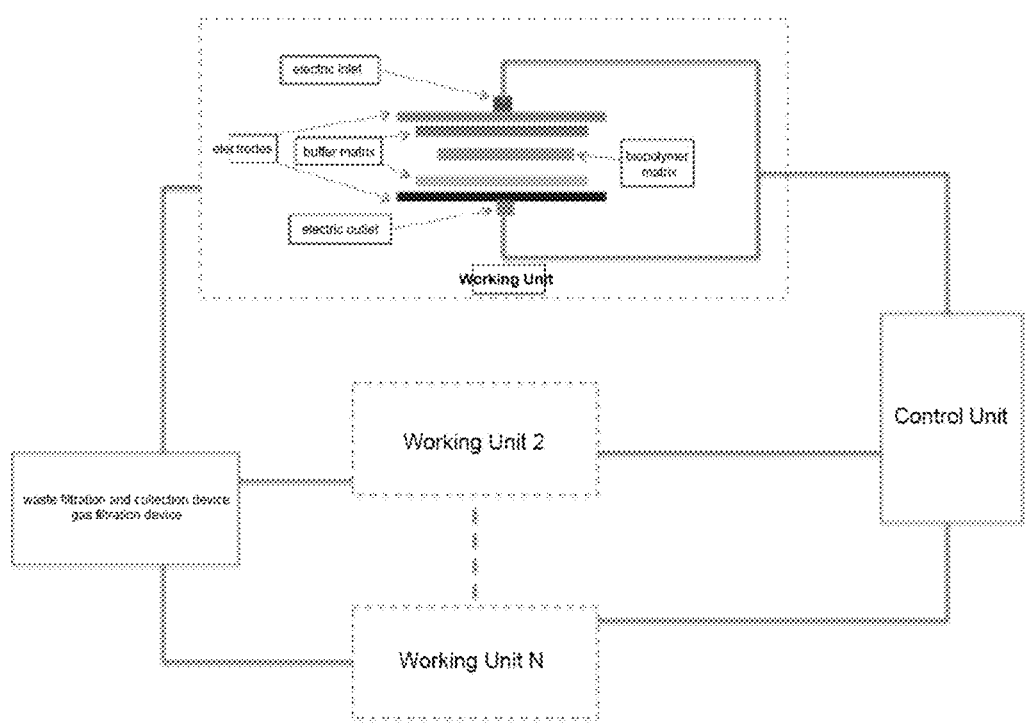
FIG. 7 schematically illustrates an automated system for implementing a staining procedure of a target molecule with a staining reagent according to an embodiment of the present invention.

Moreover, when performing the gel staining method using a system according to the present invention, gas can be generated in the staining reservoir. Accordingly, the system can further comprise a gas filtration unit to be connected to the staining reservoir, wherein the gas filtration unit can comprise a membrane or other absorbing material to remove the gas from the system. See FIG. 7, which depicts a system according to an embodiment of the present invention comprising a waste collection unit and gas filtration device. In other embodiments of the present invention, a staining reservoir can be outfitted with one or more additional components to facilitate the diffusion of gas waste out of the system. Retention of gas waste in the system can cause corrosion and shorten the lifetime of the components of the system, although a small amount of gas waste retained in the system may not be harmful to the system.

In other embodiments, a fan can be connected to the staining reservoir to facilitate diffusion of gas waste out of the system. The fan can blow gas waste generated in the staining reservoir out of the system. Alternatively, the system can be placed in a fume hood. After gas waste is blown out of the system, the gas waste can be ventilated through a fume hood. Or, the gas waste can just diffuse and dilute into the air after being blown out of the system by the fan.

In certain embodiments, a staining solution that is pumped into the staining reservoir of a system of the present invention comprises, per liter of staining solution, about 10 grams to about 300 grams acetic acid, about 10 grams to about 500 grams isopropanol, about 0.1 grams to about 10 grams EDTA, about 0.1 grams to about 10 grams Tris, about 0.1 grams to 5 grams Coomassie Blue, about 0.1 grams to about 10 grams $Na_2HPO_4$, and about 0.1 grams to about 10 grams NaCl, and the pH being in the range of about 2.0 to 11.0. In other preferred embodiments, a washing buffer that is pumped into the staining reservoir of a system of the present invention comprises, per liter of washing buffer, about 10 grams to about 300 grams acetic acid, about 10 grams to about 500 grams isopropanol, about 0.1 grams to about 10 grams EDTA, about 0.1 grams to about 10 grams Tris, about 0.1 gram to about 10 grams $Na_2HPO_4$, and about 0.1 gram to about 10 grams NaCl, and the pH being in the range of about 2.0 to about 11.0. However, any staining solutions, washing buffers, and/or other electrolytic buffers suitable for gel electrophoresis methods can be used with a system according to the present invention in view of the present disclosure.

According to embodiments of the present invention, the washing buffer that is pumped into the staining reservoir of a system of the present invention is a phosphate buffer comprising at least one of a phosphate acid and phosphate ions. In a particular embodiment, the washing buffer has a phosphate acid concentration or phosphate ion concentration between about 15 μM and about 150 mM. In a preferred embodiment, the washing buffer comprises about 25 mM $NaH_2PO_4$.

According to embodiments of the present invention, the washing buffer can further comprise EDTA. A typical concentration of EDTA that can be used in the washing buffer is about 25 mM. The washing buffer can also further comprise soluble organic ions. Examples, of soluble organic ions include, but are not limited to, formic acid, lactic acid, acetic acid, citric acid, etc., and any combination thereof. In a particular embodiment of the present invention, the washing buffer comprises about 0.1 mM to about 12 M lactic acid ions. In another particular embodiment, the washing buffer comprises about 0.1 mM to about 12 M acetic acid ions.

According to embodiments of the present invention, any of the systems described herein can be automated. An automated system according to the invention further comprises an automated control unit connected to the pair of electrodes. The automated control unit comprises one or more components selected from the group consisting of a display panel, a power supply, and a power switch.

According to embodiments of the present invention, the automated control unit can be connected to a computer interface that directs the automated control unit to control one or more parameters related to the electrophoresis staining method. For example, the automated control unit can be programmed to control run time (i.e., the amount of time in which an electric force is applied by the electrodes), voltage, current, number of run cycles, analysis and processing of input data, run start, run stop, and run pause commands, pump flow rate, etc. The aforementioned parameters can be adjusted to improve the efficiency of the staining method, and one of ordinary skill in the art could readily determine and optimize the appropriate values for each of these parameters in the automated run in order to achieve the desired results in view of the present disclosure.

According to embodiments of the present invention, the computer interface connected to the automated control unit according to an embodiment of the present invention can also be used for recording the operational log and detection data, monitoring the working status of an electrophoresis run in progress, and saving particular run methods used to operate the system for conducting an electrophoresis staining experiment. For example, the computer interface can monitor the automated system to determine if a problem occurs during an electrophoresis run, and subsequently stop the run before completion to avoid damaging the system.

According to embodiments of the present invention, an automated system can comprise a plurality of pairs of electrodes, with each pair of electrodes having a matrix embedded with a target molecule interposed therein. Each of the plurality of pairs of electrodes can be connected to the automated control unit, and electrophoresis of each can be done independently or simultaneously according to the parameters as directed by the automated control unit. See, e.g., FIG. 7, which depicts an automated system according to an embodiment of the present invention comprising an automated control unit connected to a plurality of pairs of electrodes, referred to in the figure as "working units."

According to embodiments of the invention, the electrodes can be directly or indirectly connected to an electrical inlet/outlet. For example, electrodes can be indirectly connected through wires or contacts made of conductive materials. The electrodes can be connected via the electrical inlet/outlet to an automated control unit as described herein, or they can be connected via the electrical inlet/outlet to any other suitable external power source.

In certain embodiments, the pair of electrodes of the system is assembled in a working unit. The working unit can be connected to an automated control system, or to any other suitable external power source. If the electrodes are directly connected to an electrical inlet/outlet, the electrode plates are preferably bound within the working unit. If the electrode plates are indirectly connected to an electrical inlet/outlet, the working unit can be designed with a holding portion to position and secure the electrode plates in place, and the holding portion can be configured with the electrical inlet/outlet. A person of ordinary skill in the art will be familiar with such working units and apparatus used for electrophoresis.

According to embodiments of the invention, a system can further comprise a pressure providing mechanism to hold the pair of electrodes together and secure the matrix embedded with the target molecule therein. The pressure providing mechanism is not limited in any way, and can employ a deformation mechanism including, but not limited to springs and sponges, or an oscillation mechanism including, but not limited to, cams. Clamps can also be employed to hold the electrodes together with the matrix interposed therein. Deformation devices, such as springs and sponges, can be mounted on the backsides of electrode plates, or on the holding portion of a working unit that secures the electrode plates in position. The pressure provided between the two electrodes can be an inward pressure, or an outward pressure. When the electrode plates are placed horizontally, the weight of the upper electrode plate can be increased to create a pressure providing mechanism.

According to particular embodiments of the present invention, a system for staining a target molecule comprises, in the following order:
  (i) a first solid porous material absorbed with a staining solution comprising a staining reagent;
  (ii) a matrix embedded with the target molecule;
  (iii) a second solid porous material absorbed with an electrolytic buffer; and
  (iv) a pair of electrodes for applying an electric force sufficient to move the staining reagent from the first solid porous material into the matrix embedded with the target molecule, thereby staining the target molecule, and to move excess free staining reagent out of the matrix, thereby destaining the matrix;
wherein the pair of electrodes are connected to the first solid porous material and second solid porous material, respectively. In certain embodiments, such system is an automated system, wherein an automated control unit is connected to the pair of electrodes.

According to embodiments of the present invention, the system can further comprise a third solid porous material to be absorbed with a washing buffer. The third solid porous material is to placed adjacent to the first solid porous material, such that the pair of electrodes are to be connected to the third solid porous material absorbed with the washing buffer and the second solid porous material absorbed with the electrolytic buffer. A purpose of the third solid porous material absorbed with a washing buffer is to aid in destaining of the matrix. However, embodiments of the invention are not limited to systems comprising three separate solid porous materials, but also relate to embodiments with more than three separate solid porous materials absorbed with the appropriate buffer solutions to optimize the electrophoresis staining method.

In other particular embodiments of the system, the first solid porous material is absorbed with a staining solution, wherein the staining solution comprises, per liter of staining solution, about 10 grams to about 300 grams acetic acid, about 10 grams to about 500 grams isopropanol, about 0.1 grams to about 10 grams EDTA, about 0.1 gram to about 10 grams Tris, about 0.1 gram to 5 grams Coomassie Blue, about 0.1 gram to about 10 grams $Na_2HPO_4$, and about 0.1 gram to about 10 grams NaCl, and the pH being in the range of about 2.0 to about 11.0; and the second porous material is absorbed with an electrolytic buffer, the electrolytic buffer comprising, per liter of electrolytic buffer, about 1 gram to about 50 grams sodium phosphate, monobasic, and the pH being in the range of about 2.0 to about 10.0. In embodiments where the system further comprises a third solid porous material absorbed with a washing buffer, the washing buffer comprises, per liter of washing buffer, about 10 grams to about 300 grams acetic acid, about 10 grams to about 500 grams isopropanol, about 0.1 grams to about 10 grams EDTA, about 0.1 gram to about 10 grams Tris, about 0.1 gram to about 10 grams $Na_2HPO_4$, and about 0.1 gram to about 10 grams NaCl, and the pH being in the range of about 2.0 to about 11.0

Any matrix, stain, staining solution, and buffer solution can be used with a system of the present invention in view of the present disclosure. Systems according to the present invention can also be used to stain any target molecule in view of the present disclosure. In particularly preferred embodiments of a system according to the present invention, the matrix is a polyacrylamide gel; the target molecule embedded in the matrix is a biopolymer, and is more preferably a peptide or protein; and the staining reagent is Coomassie Blue.

The invention also provides kits comprising one or more components useful for performing staining or binding assays and instructions for using the components in carrying out a method of the invention. In one embodiment, the kit is compartmentalized to receive the one or more components. In yet another embodiment, the kit can comprise a device for performing quick protein staining assays.

According to embodiments of the present invention, a system can further comprise any of the kits described herein. In particular, the systems of the present invention can further comprise kits that contain staining solutions, solid porous materials, buffer solutions (e.g., washing buffer, electrolytic buffer), and/or matrices for embedding a target molecule, etc., wherein the components of the kit can be used with the system for performing a gel staining method according to the present invention.

In an embodiment of the present invention, the kit comprises staining solutions and optionally one or more other buffer solutions and instructions for using the solutions in a quick biopolymer staining assay according to an embodiment of the invention. The solutions can be provided in the kit in bottles or containers. The solutions can also be provided in the kit in solid porous materials, such as in pads, pre-absorbed with the solutions.

According to particular embodiments of the present invention, a kit for staining a target molecule embedded in a matrix with a staining reagent comprises:
  (i) a staining solution comprising a staining reagent;
  (ii) a plurality of solid porous materials;
  (iii) optionally one or more buffer solutions;
  (iv) optionally one or more matrices for embedding a target molecule; and
  (v) instructions for using the staining the solution and optionally the buffer solutions for staining the biopolymer in the matrix utilizing an electric force applied to the staining reagent.

In particularly preferred embodiments of the present invention, the staining solution and buffer solution are pre-absorbed in separate solid porous materials. In other particularly preferred embodiments of the kit, the solid porous material is a blotting paper having a thickness of about 0.1 mm to about 20 mm. Any of the kits disclosed and described herein can be part of a system for staining a target molecule according to embodiments of the present invention.

In other general aspects of the present invention, biopolymers other than peptides or proteins can also be stained using similar methods in view of the present disclosure. For example, an RNA, a DNA or a complex containing DNA or RNA, embedded in a matrix, such as an agarose gel or a polyacrylamide gel, can be stained by a staining reagent for nucleotides, such as an intercalating dye, preferably an intercalating fluorescent dye, using methods of the invention. Examples of the intercalating dyes include, but are not limited to, fluorescent dyes SYTO 61 (Invitrogen Corporation) and TOTO-3 (Invitrogen Corporation), ethidium bromide or propidium iodide.

In another embodiment of the present invention, an RNA, a DNA or a complex containing DNA or RNA, embedded in a matrix can be labeled by a labeling polynucleotide, e.g., a labeled polynucleotide probe, using a method according to the present invention. For example, an electric force can be applied to the labeled probe to move it into the matrix embedded with the DNA, the RNA, or the complex, to thereby hybridize with the DNA, the RNA or the complex in the matrix with reduced time.

It is readily appreciated by those skilled in the art that, similar methods can also be generally applied for interacting, reacting, binding or staining of a target molecule with a charged molecule. The target molecule is embedded in a matrix. An electric force moves the charged molecule into the matrix to thus interact, react, bind or stain the target molecule in the matrix.

The electrodes used in the methods and systems of the present invention can be made of any suitable material known and used in the art. For example, the electrodes can be made from copper, iron, graphite, or stainless steel. The electrodes can also be coated with an inert metal including, but not limited to, platinum and titanium.

The systems and kits for staining a target molecule of the present invention described herein are different from other staining systems known and used in the field of electrophoresis, such as systems and kits for performing Western Blot transfer. In a typical set-up used for Western Blot transfer, a protein is transferred from a gel matrix onto a membrane. The membrane with the transferred protein is then subsequently treated to detect the protein. In contrast, in one embodiment, a system for staining a target molecule according to embodiments of the present invention uses an electric force to transfer a staining reagent (e.g., dye) from a solid porous material into a matrix embedded with a target molecule, and transfer excess free staining reagent out of the matrix. In another embodiment, also in contrast to a typical set-up used for Western Blot transfer, a system for staining a target molecule according to the present invention uses a pump for pumping a staining solution comprising a staining reagent into a staining reservoir containing a matrix embedded with the target molecule and an electric force to move the staining reagent from the staining solution into the matrix and excess free staining reagent out of the matrix, thereby staining the target molecule and destaining the matrix.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples are further illustrative of the nature of the invention, it needs to be understood that the invention is not limited thereto.

EXAMPLE

Protein Staining

Protein markers (GenScript MM0900) and bovine serum albumin (BSA) at various amounts, 1500 ng, 750 ng, 300 ng, 150 ng, 75 ng and 30 ng were loaded onto two mini SDS-PAGE gels in Lane M, Lane 1, Lane 2, Lane 3, Lane 4, Lane 5 and Lane 6, respectively. Electrophoresis was conducted to separate and embed the markers and BSA in the gels.

After the electrophoresis, one gel was stained using the quick staining procedure according to an embodiment of the present invention. The SDS-PAGE apparatus was disassembled. A quick staining system as shown in FIG. 5 was assembled. Buffer A contains, per liter of Buffer A, 200 grams acetic acid, 250 grams isopropanol, 10 grams EDTA, 6 grams Tris, and the pH is about 3.5. Buffer B contains 0.5% (wt/wt) of Coomassie blue R-250 in addition to the other ingredients of Buffer A. Buffer C contains, per liter of Buffer C, 20 grams sodium phosphate, monobasic, and 1 gram EDTA, and the pH is about 6.5. Electricity was applied to the quick staining system via the electrodes. The staining procedure was conducted at 20 volts for 6 minutes. FIG. 3 is a picture of the gel stained by Coomassie Blue using the quick staining procedure, which took only about 6 minutes.

Figure 4:
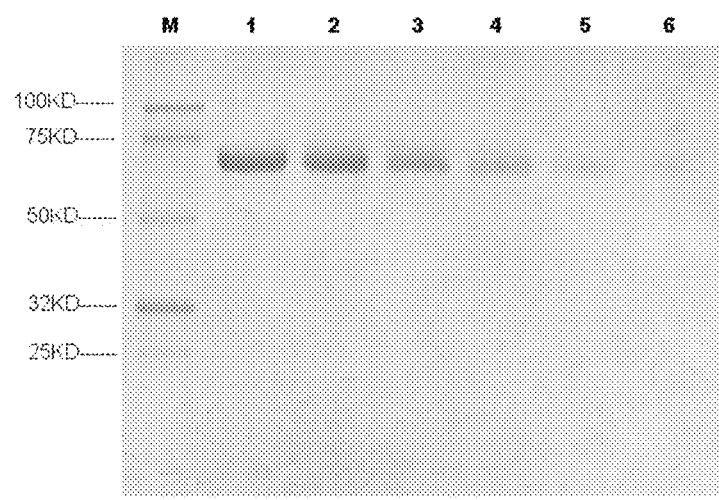
FIG. 4 is a picture of a SDS-PAGE gel after the conventional Coomassie Blue staining procedure of FIG. 1; the gel is embedded with protein markers (GenScript MM0900; Lane M) and BSA protein at 1500 ng, 750 ng, 300 ng, 150 ng, 75 ng and 30 ng, in lanes 1 to 6, respectively.

After the electrophoresis, another gel was stained using the conventional staining procedure. The SDS-PAGE apparatus was disassembled. The gel was fixed in a gel-fixing solution (100 ml of 10% acetic acid and 20% methanol in water) for 1 hr with gentle agitation. At the end of fixing, the gel-fixing solution was removed and the gel was washed with deionized water. Staining solution (0.1% Coomassie blue R-250, 25% methanol and 10% acetic acid in water), 100 ml, was added to the gel. The gel was stained for 1 hr with gentle agitation. The staining solution was removed, and the gel was washed with deionized water. Destaining solution (25% methanol and 10% acetic acid in water), 100 ml, was added to the gel to destain the gel for 1 hr with gentle agitation. The destaining step was repeated 3 times until the protein bands were seen without background. FIG. 4 is a picture of the gel stained by Coomassie Blue using the conventional staining procedure, which took about 5 hours, 50 times of that used in the quick staining method.

FIGS. 3 and 4 show that the quick staining method according to an embodiment of the present invention achieved comparable results as that obtained by the conventional staining method, but in drastically reduced amount of time.

FIG. 6 illustrates an alternative quick staining system, which is similar to that illustrated in FIG. 5, except that the blotting paper presoaked in Buffer A is omitted. FIG. 6 illustrates an automated system for quick staining that can be used with either embodiment shown in FIG. 5 and FIG. 6.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

We claim:

1. A system for staining a target molecule with a staining reagent, wherein the system comprises:
   (i) a pair of electrodes; and
   (ii) a staining system interposed between the pair of electrodes, the staining system comprising, from one electrode of the pair of electrodes to the other electrode, in the following order:
   (a) a third solid porous material absorbed with a washing buffer;
   (b) a first solid porous material absorbed with a staining solution comprising the staining reagent;
   (c) a matrix embedded with the target molecule; and
   (d) a second solid porous material absorbed with an electrolytic buffer;

wherein the pair of electrodes is for applying an electric force sufficient to move the staining reagent from the first solid porous material into the matrix embedded with the target molecule, thereby staining the target molecule, and to move excess free staining reagent out of the matrix, thereby destaining the matrix and the pair of electrodes are to be connected to the third solid porous material and second solid porous material, respectively; and wherein:

the staining solution comprises, per liter of the staining solution, about 10 grams to about 300 grams acetic acid, about 10 grams to about 500 grams isopropanol, about 0.1 grams to about 10 grams EDTA, about 0.1 gram to about 10 grams Tris, about 0.1 gram to 5 grams Coomassie Blue, about 0.1 gram to about 10 grams $Na_2HPO_4$, and about 0.1 gram to about 10 grams NaCl, and the pH being in the range of about 2.0 to about 11.0;

the electrolytic buffer comprises, per liter of electrolytic buffer, about 1 gram to about 50 grams sodium phosphate, monobasic, and the pH being in the range of about 2.0 to about 10.0; and the washing buffer comprises, per liter of washing buffer, about 10 grams to about 300 grams acetic acid, about 10 grams to about 500 grams isopropanol, about 0.1 grams to about 10 grams EDTA, about 0.1 gram to about 10 grams Tris, about 0.1 gram to about 10 grams $Na_2HPO_4$ and about 0.1 gram to about 10 grams NaCl, and the pH being in the range of about 2.0 to about 11.0.

2. The system according to claim 1, wherein the matrix embedded with the target molecule and the first solid porous material are interposed between the pair of electrodes, such that the electric force moves the staining reagent in a direction such that the excess free staining reagent enters the matrix and travels the least distance in the matrix before leaving the matrix as compared to the other directions.

3. The system according to claim 1, wherein the matrix is selected from the group consisting of an agarose gel, a polyacrylamide gel, and any porous material capable of being embedded with a target molecule; the target molecule is a biopolymer selected from the group consisting of a peptide, a protein, an RNA, a DNA, an oligosaccharide, and a complex thereof; and the staining reagent is a charged molecule selected from the group consisting of an organic or inorganic reagent, a dye or a dye-labeled reagent, a fluorescent molecule, a metal-complex dye, a radioactive or radioactive-labeled reagent, an antibody or an antibody-based reagent, a labeled peptide or ligand, and a labeled polynucleotide.

4. The system according to claim 1, wherein the matrix is a polyacrylamide gel embedded with a protein or peptide.

* * * * *